(12) United States Patent
Oyama

(10) Patent No.: US 12,089,806 B2
(45) Date of Patent: Sep. 17, 2024

(54) IMAGE RECORDING APPARATUS, RECORDING METHOD, AND IMAGE RECORDING SYSTEM

(71) Applicant: OLYMPUS CORPORATION, Tokyo (JP)

(72) Inventor: Masatsugu Oyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 355 days.

(21) Appl. No.: 17/493,056

(22) Filed: Oct. 4, 2021

(65) Prior Publication Data

US 2022/0022727 A1 Jan. 27, 2022

Related U.S. Application Data

(63) Continuation of application No. PCT/JP2019/014945, filed on Apr. 4, 2019.

(51) Int. Cl.
*A61B 1/00* (2006.01)
*G16H 10/60* (2018.01)
*H04N 5/77* (2006.01)

(52) U.S. Cl.
CPC ........... *A61B 1/0002* (2013.01); *G16H 10/60* (2018.01); *H04N 5/772* (2013.01)

(58) Field of Classification Search
CPC ....... A61B 1/0002; G16H 10/60; H04N 5/772
See application file for complete search history.

(56) References Cited

U.S. PATENT DOCUMENTS

2021/0065746 A1* 3/2021 Sugano ................ G11B 27/031

FOREIGN PATENT DOCUMENTS

| JP | 2002-272758 A | 9/2002 |
|---|---|---|
| JP | 2011-041585 A | 3/2011 |
| JP | 5851647 B2 | 2/2016 |
| JP | 2017-006384 A | 1/2017 |
| JP | 2017118913 A * | 7/2017 |
| JP | 6369706 B1 | 8/2018 |

OTHER PUBLICATIONS

International Search Report dated May 28, 2019 issued in PCT/JP2019/014945.
English Abstract of EP 3005935 A1 dated Apr. 13, 2016.

* cited by examiner

*Primary Examiner* — Girumsew Wendmagegn
(74) *Attorney, Agent, or Firm* — Scully, Scott, Murphy & Presser, P.C.

(57) ABSTRACT

An image recording apparatus includes a recording section, a storage section, and a control section. The recording section records an output video outputted from a first endoscope, an output video outputted from a PACS terminal, and an output video outputted from a second endoscope, and generates recording information including data of the output videos, to retain the generated recording information. The storage section stores display state information outputted from a display apparatus. The control section controls the recording section and the storage section, so as to generate the recording information by associating the data of the output videos with the display state information.

13 Claims, 9 Drawing Sheets

FIG. 7

| | | | | | |
|---|---|---|---|---|---|
| OUTPUT VIDEO | S2 | S1 | S2 | S3 | S1, S3 |
| EDITING POINT | Index A | Index B | Index C | Index D | Index E |
| TIME | 00:00:00 | 00:10:05 | 01:05:12 | 01:15:30 | 01:45:20 |
| VIDEO INPUT APPARATUS | PACS | SURGICAL ENDOSCOPE | PACS | GASTROINTESTINAL ENDOSCOPE | SURGICAL ENDOSCOPE GASTROINTESTINAL ENDOSCOPE |
| INPUT TERMINAL | Y/C 1 | SDI 1 | Y/C 1 | SDI 2 | SDI 1 SDI 2 |
| GAMMA | DICOM | Endoscope 1 | DICOM | Endoscope 2 | Endoscope 1 Endoscope 2 |
| CONTRAST | 70 | 50 | 70 | 50 | 50 |
| BRIGHTNESS | 80 | 80 | 80 | 80 | 80 |
| COLOR TEMPRATURE | 6500K | 6500K | 6500K | 9300K | 6500K |
| SCAN MODE | OFF | OFF | OFF | 2 | OFF |
| TWO-SCREEN DISPLAY | OFF | OFF | OFF | OFF | POP |

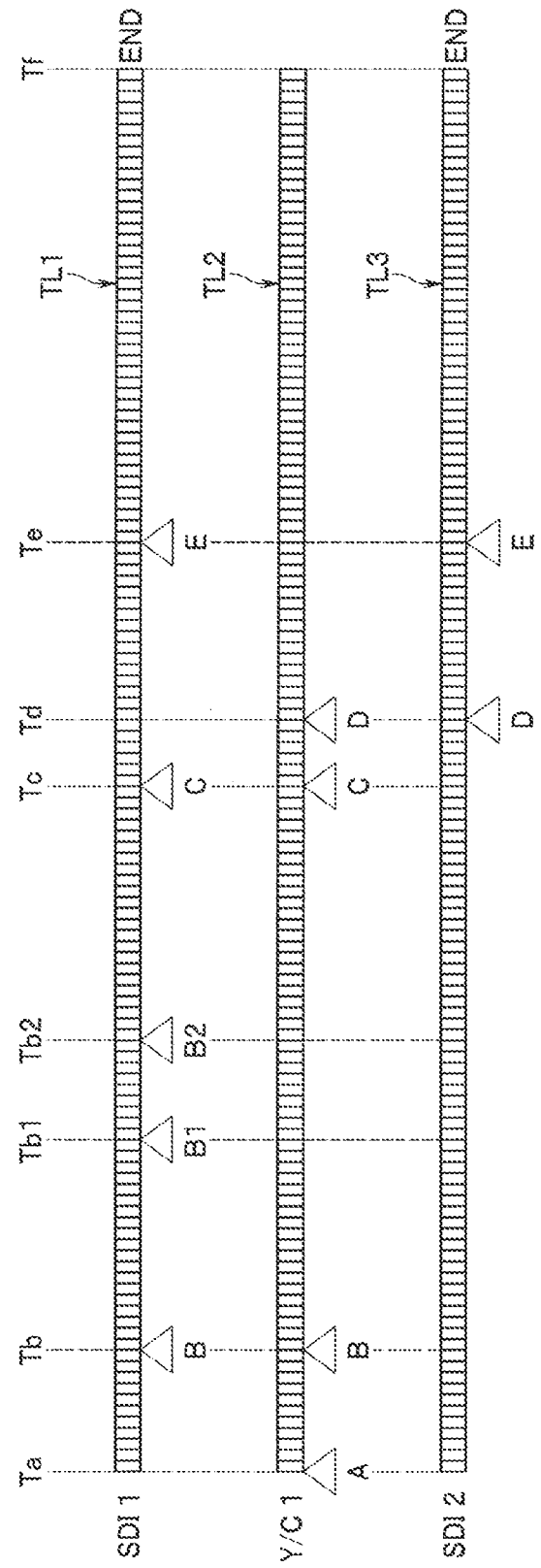

IMAGE RECORDING APPARATUS, RECORDING METHOD, AND IMAGE RECORDING SYSTEM

CROSS-REFERENCE TO RELATED APPLICATION

This application is a continuation application of PCT/JP2019/014945 filed on Apr. 4, 2019, the entire contents of which are incorporated herein by this reference.

BACKGROUND OF THE INVENTION

1. Field of the Invention

The present invention relates to an image recording apparatus, a recording method, and an image recording system that are for recording a plurality of output videos outputted from a plurality of video output apparatuses.

2. Description of the Related Art

In the medical sites, various kinds of medical modalities are used for generating medical images for diagnosis. Examples of the medical modalities include an endoscope that generates endoscopic images, an MRI apparatus that generates MRI images, a CT apparatus that generates CT images, and the like. As disclosed in Japanese Patent Application Laid-Open Publication No. 2017-6384, for example, the medical modalities are configured to be capable of displaying, saving, and transmitting medical images.

In recent years, medical image management systems called PACS (Picture Archiving and Communication Systems) have been developed. Such medical image management systems are configured to manage a plurality of medical images generated by a plurality of medical modalities. A known PACS is, as disclosed in Japanese Patent Application Laid-Open Publication No. 2011-41585, for example, provided with a server for storing a plurality of medical images and an image viewer terminal for displaying the plurality of medical images.

One example of a surgical system provided with medical modalities is an endoscopic surgical system configured to perform medical procedures by using an endoscope. The endoscopic surgical system is provided with a display apparatus configured to display endoscopic images picked up by the endoscope. A known example of a display apparatus of an endoscopic surgical system includes a monitor apparatus disclosed in Japan Patent No. 5851647. The monitor apparatus is configured to be capable of receiving not only endoscopic images, but also videos corresponding to medical images outputted from a plurality of medical modalities other than the endoscope and videos corresponding to medical images outputted from PACS terminals.

SUMMARY OF THE INVENTION

An image recording apparatus according to one aspect of the present invention is an image recoding apparatus including a processor that includes hardware. The processor is configured to: record a plurality of output videos outputted from a plurality of video output apparatuses, and generate recording information including data of the plurality of output videos, to retain the generated recording information; store display state information outputted from a display apparatus configured to display the plurality of output videos, the display state information relating to change points of display states of the plurality of output videos in the display apparatus; and generate the recording information by associating the data of the plurality of output videos with the display state information.

A recording method according to one aspect of the present invention is a recording method for recording output video signals from video output apparatuses. The recording method includes: recording a plurality of output videos outputted from a plurality of video output apparatuses, and generating recording information including data of the plurality of output videos, to retain the generated recording information; storing display state information outputted from a display apparatus configured to display the plurality of output videos, the display state information relating to change points of display states of the plurality of output videos in the display apparatus; and generating the recording information by associating the data of the plurality of output videos with the display state information.

An image recording system according to one aspect of the present invention is an image recording system including video output apparatuses that output video signals, a processor that processes the video signals, and a display apparatus that displays output videos outputted from the processor. The processor is configured to: record a plurality of output videos outputted from a plurality of video output apparatuses, and generate recording information including data of the plurality of output videos, to retain the generated recording information; store display state information outputted from the display apparatus, the display state information relating to change points of display states of the plurality of output videos in the display apparatus; and generate the recording information by associating the data of the plurality of output videos with the display state information.

BRIEF DESCRIPTION OF THE DRAWINGS

FIG. 7 is a chart showing an example of display state information in the embodiment of the present invention.

FIG. 9 is an explanatory view for explaining editing points imparted to data of a plurality of output videos in a modification of the embodiment of the present invention.

DETAILED DESCRIPTION OF THE PREFERRED EMBODIMENT(S)

Hereinafter, an embodiment of the present invention will be described with reference to drawings.

(Configuration of Endoscopic Surgical System)

Figure 1:
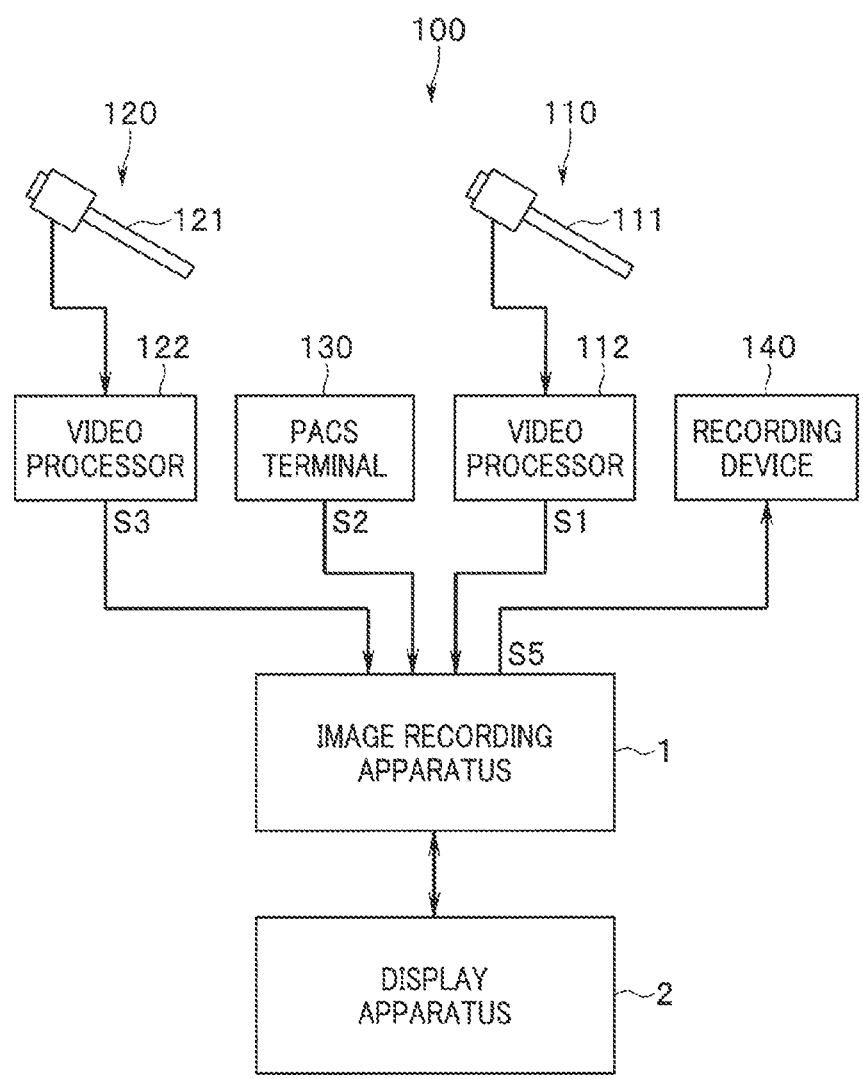
FIG. 1 is an explanatory diagram showing a configuration of an endoscopic surgical system in an embodiment of the present invention.

First, description will be made on a configuration of a system including an image recording apparatus according to an embodiment of the present invention. An image recording apparatus 1 according to the present embodiment is an image recording apparatus for medical use. FIG. 1 shows a configuration of an endoscopic surgical system 100 provided with the image recording apparatus 1 according to the present embodiment. The endoscopic surgical system 100 includes a plurality of video output apparatuses that are connected to the image recording apparatus 1, a display apparatus 2, and a recording device 140, in addition to the image recording apparatus 1. The display apparatus 2 is an apparatus for displaying a plurality of output videos outputted from the plurality of video output apparatuses.

The recording device 140 is an apparatus or a recording medium that records recording information to be described later. As the recording device 140, an optical drive apparatus configured to record information on an optical disk such as an CD, a DVD, a Blu-ray disk, etc., a hard disk apparatus configured to record information on a magnetic disk, or a semiconductor memory apparatus, such as a USB memory, configured to record information in a flash memory, is used, for example.

Here, it is supposed that there is a group of a plurality of apparatuses including: a plurality of medical modalities each of which is configured to generate medical images for diagnosis; and a medical image management apparatus configured to manage the medical images. The plurality of video output apparatuses in the present embodiment are selected from the group of the plurality of apparatuses. In the present embodiment, a first endoscope 110 and a second endoscope 120, which are medical modalities, and a terminal of a medical image management apparatus (hereinafter referred to as a PACS terminal) 130 are connected to the image recording apparatus 1.

The first endoscope 110 includes an endoscope main body 111 and a video processor 112. The endoscope main body 111 is configured to pick up an image of an object to generate an endoscopic image, and transmit the generated endoscopic image to the video processor 112 by wired or wireless communication. The video processor 112 is configured to perform predetermined image processing on the endoscopic image to generate a video of the object, and output to the image recording apparatus 1 the generated video as an output video S1.

The second endoscope 120 has the same configuration as that of the first endoscope 110. In other words, the second endoscope 120 includes an endoscope main body 121 and a video processor 122. The endoscope main body 121 is configured to pick up an image of an object to generate an endoscopic image, and transmits the generated endoscopic image to the video processor 122 by wired or wireless communication. The video processor 122 is configured to perform predetermined image processing on the endoscopic image to generate a video of the object, and output to the image recording apparatus 1 the generated video as an output video S3.

The PACS terminal 130 is an apparatus configured to output to the image recording apparatus 1 medical images as an output video S2. The medical images include MRI images, CT images, and the like stored in the medical image management system called PACS (Picture Archiving and Communication Systems). Note that the medical images such as MRI images, CT images, and the like are photographed, in advance, by an MRI apparatus, a CT apparatus, and the like, before a surgery using the endoscopic surgical system 100.

(Configuration of Image Recording Apparatus)

Figure 2:
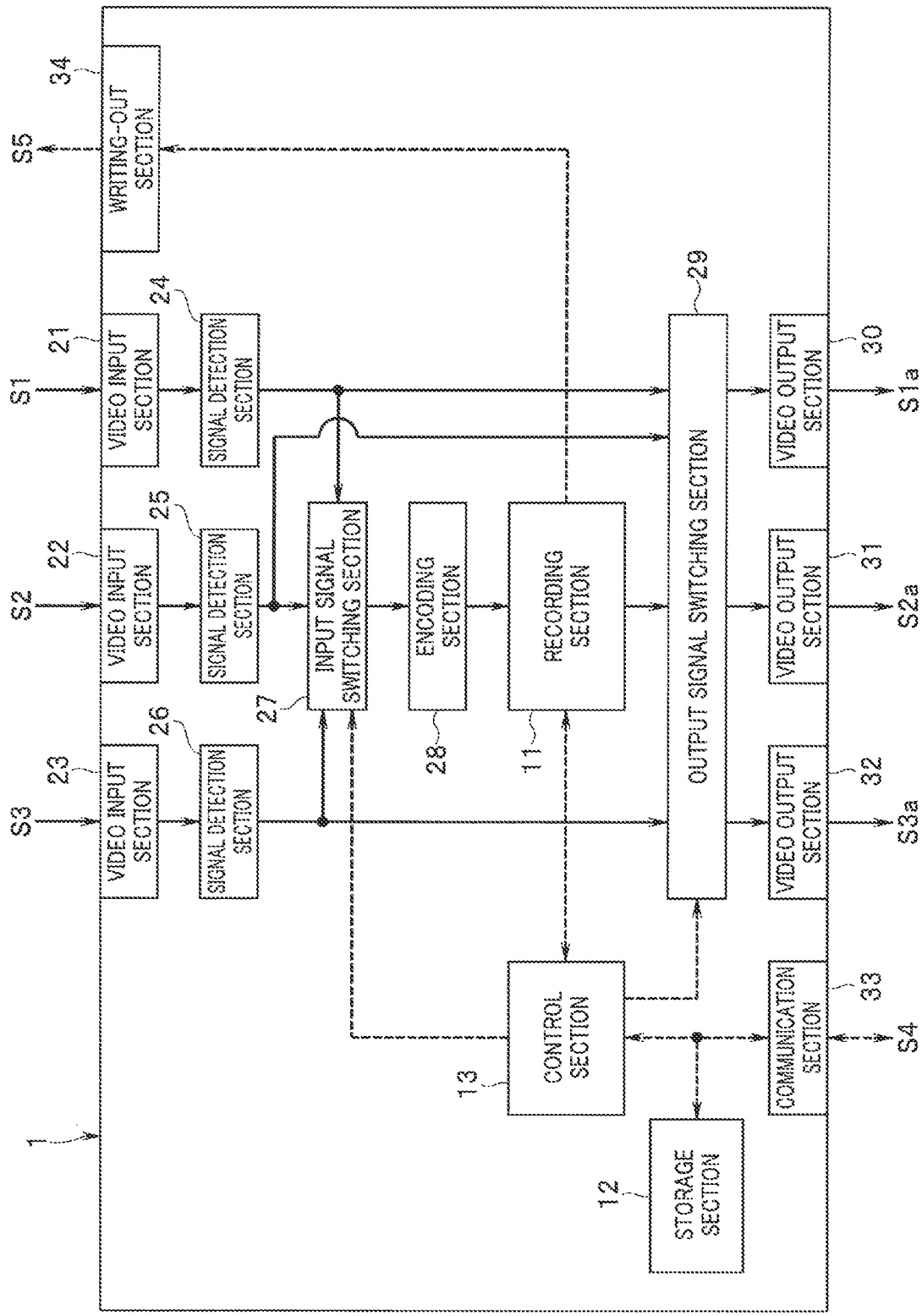
FIG. 2 is a functional block diagram showing a configuration of an image recording apparatus according to the embodiment of the present invention.

Next, description will be made on the configuration of the image recording apparatus 1, with reference to FIG. 2. FIG. 2 is a functional block diagram showing the configuration of the image recording apparatus 1. First, description will be made on a main part of the image recording apparatus 1. The image recording apparatus 1 includes, as the main part, a recording section 11, a storage section 12, and a control section 13.

The recording section 11 is configured to record a plurality of output videos that are outputted from the plurality of video output apparatuses, and generate recording information including data of the plurality of output videos, to retain the generated recording information. The recording section 11 generates the recording information by associating the data of the plurality of output videos with time information having a correspondence with a lapse of time. The time information may be information of clock time, or an elapsed time from the clock time at which the recording of the plurality of output videos was started. The recording section 11 is configured to be capable of outputting at least a part of the recording information.

The storage section 12 is configured to store display state information outputted from the display apparatus 2. The display state information relates to display states of the plurality of output videos in the display apparatus 2. The storage section 12 stores the display state information in association with the time information, similarly as the recording information. The display state information includes information on the input source of each of the plurality of output videos in the display apparatus 2, information on correction parameters for each of the plurality of output videos in the display apparatus 2, and information on a display style of each of the plurality of output videos in the display apparatus 2.

In addition, the display state information includes a plurality pieces of setting value information for identifying the plurality of video output apparatuses. The storage section 12 further stores a table showing a correspondence between the plurality of video output apparatuses and the plurality of pieces of setting value information. The table is created in advance before the surgery using the endoscopic surgical system 100.

The control section 13 controls the recording section 11 and the storage section 12 so as to generate recording information by associating the data of the plurality of output videos with the display state information. In addition, the control section 13 controls the recording section 11 and the storage section 12 so as to identify the output source of each of the plurality of output videos by using the table stored in the storage section 12 and add the information on the identified output source to the data of each of the plurality of output videos.

Furthermore, the control section 13 is capable of causing the plurality of output videos, which are included in the recording information retained in the recording section 11, to be displayed on the display apparatus 2, and causing a screen for editing the recording information retained in the recording section 11 to be displayed on the display apparatus 2, and causing at least a part of the recording information retained in the recording section 11 to be recorded in a recording device 140 or on a recording medium of the recording device 140.

As described above, in the present embodiment, the plurality of video output apparatuses are the first and second endoscopes 110, 120, and the PACS terminal 130, as shown in FIG. 1, and the plurality of output videos are the output videos S1 to S3. In the present embodiment, the recording section 11 records the output videos S1 to S3, and generates the recording information including the data of the output videos S1 to S3, to retain the generated recording information. Furthermore, the control section 13 generates the recording information by associating the data of the output videos S1 to S3 with the display state information.

Next, description will be made on a configuration of other parts, other than the main part, of the image recording apparatus 1. The image recording apparatus 1 further includes three video input sections 21, 22, 23, and three signal detection sections 24, 25, 26, an input signal switching section 27, an encoding section 28, an output signal switching section 29, three video output sections 30, 31, 32, a communication section 33, and a writing-out section 34.

Each of the video input sections 21 to 23 includes an input terminal configured to receive input of the output video. Examples of the terminals used as the input terminals include a serial digital interface terminal (hereinafter, referred to as an SDI terminal), a luminance signal/chrominance signal separation terminal (hereinafter, referred to as a Y/C terminal), and the like. The video input section 21 receives an input of the output video S1 outputted from the first endoscope 110 (see FIG. 1). The video input section 22 receives an input of the output video S2 outputted from the PACS terminal 130 (see FIG. 1). The video input section 23 receives an input of the output video S3 outputted from the second endoscope 120 (see FIG. 1).

The signal detection section 24 detects presence or absence of the input of the output video S1 to the video input section 21, and outputs the output video S1 inputted to the video input section 21 to the input signal switching section 27 and the output signal switching section 29. The signal detection section 25 detects presence or absence of the input of the output video S2 to the video input section 22, and outputs the output video S2 inputted to the video input section 22 to the input signal switching section 27 and the output signal switching section 29. The signal detection section 26 detects presence or absence of the input of the output video S3 to the video input section 23, and outputs the output video S3 inputted to the video input section 23 to the input signal switching section 27 and the output signal switching section 29.

The input signal switching section 27 is configured to be controlled by the control section 13, and to select any of the inputted output videos S1 to S3 and output the selected video to the encoding section 28. The encoding section 28 converts the inputted output video into video data in a predetermined format, and outputs to the recording section 11 the video data subjected to the conversion. Note that the conversion processing on the video data in the encoding section 28 may include compression processing for compressing the amount of the data. The recording section 11 records the video data subjected to the conversion in the encoding section 28, as the output video outputted from the video output apparatus.

Note that the input signal switching section 27 and the encoding section 28 may operate so as to convert only some of the output videos that satisfy a predetermined condition into video data, may operate so as to convert all of the output videos inputted to the image recording apparatus 1 into video data, or may operate so as to concurrently convert some of the output videos that satisfy the predetermined condition and all of the output videos into video data. For example, the predetermined condition may be a condition that the output video is a video that is being displayed on the display apparatus 2 when the output video is selected.

The output signal switching section 29 is configured to be controlled by the control section 13, and to select the output source of the output video, from the signal detection sections 24 to 26 and the recording section 11 and output the output video outputted from the selected output source to any one of the video output sections 30 to 32. Specifically, the output signal switching section 29 selects, as the output source of the output video S1, either the signal detection section 24 or the recording section 11, and outputs the output video S1 to the video output section 30. Further, the output signal switching section 29 selects, as the output source of the output video S2, either the signal detection section 25 or the recording section 11, and outputs the output video S2 to the video output section 31. Furthermore, the output signal switching section 29 selects, as the output source of the output video S3, either the signal detection section 26 or the recording section 11, and outputs the output video S3 to the video output section 32.

The video output section 30 outputs the output video S1 to the display apparatus 2 (see FIG. 1). The video output section 31 outputs the output video S2 to the display apparatus 2. The video output section 32 outputs the output video S3 to the display apparatus 2. Hereinafter, when the output videos S1, S2, and S3 that are outputted respectively from the video output sections 30, 31, and 32 are discriminated from the output videos S1, S2, and S3 in the image recording apparatus 1, the output videos S1, S2, and S3 that are outputted respectively from the video output sections 30, 31, and 32 are denoted by the symbols S1a, S2a, and S3a, respectively.

Each of the video output sections 30 to 32 includes an output terminal through which the output video is outputted. Examples of the terminals used as the output terminals include an SDI terminal, Y/C terminal, and the like.

Figure 3:
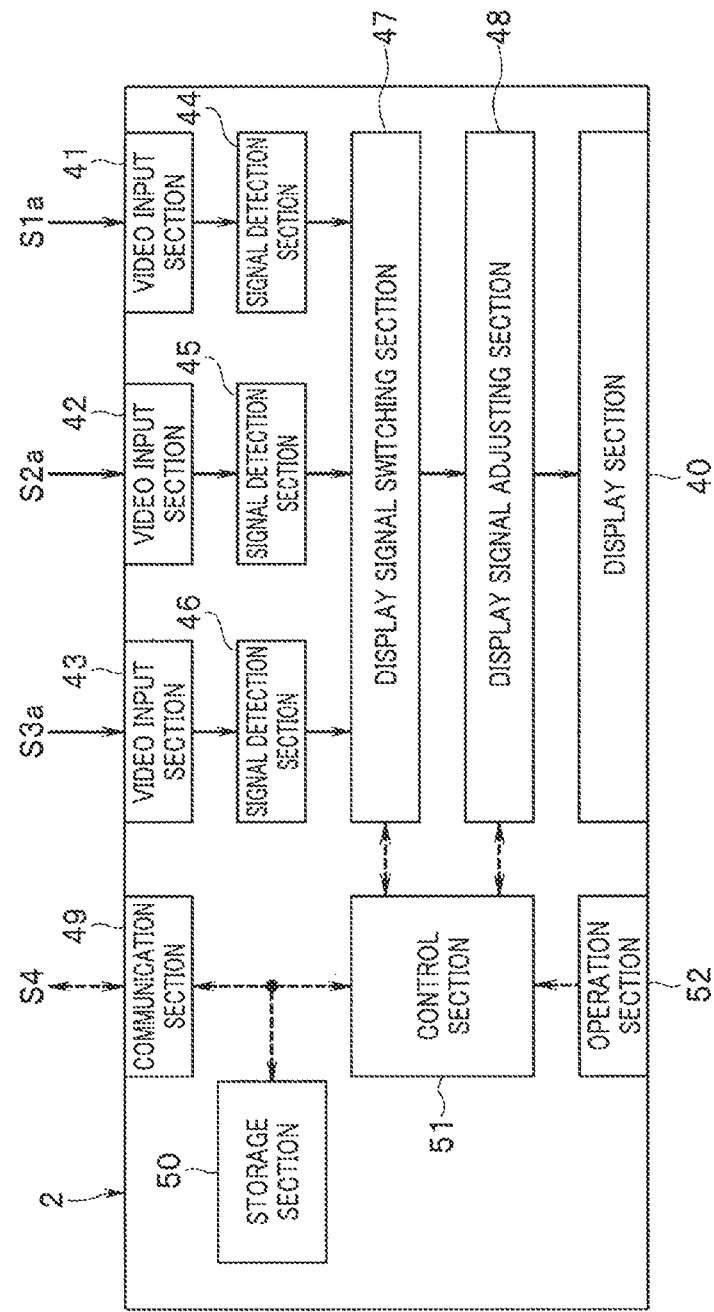
FIG. 3 is a functional block diagram showing a configuration of a display apparatus in the embodiment of the present invention.

The communication section 33 is configured to be controlled by the control section 13, and to transmit and receive predetermined information to and from the display apparatus 2. The predetermined information includes the above-described display state information. The communication section 33 outputs the received display state information to the storage section 12. The storage section 12 stores the display state information. When causing the plurality of output videos, which are included in the recording information retained in the recording section 11, to be displayed on the display apparatus 2, the communication section 33 outputs the display state information included in the recording information to the display apparatus 2. In FIG. 2 and FIG. 3 to be described later, the information transmitted and received between the communication section 33 and the display apparatus 2 is denoted by the symbol S4.

The writing-out section 34 is configured to output at least a part of the recording information retained in the recording section 11 to the recording device 140 (see FIG. 1). At least a part of the recording information can be recorded, that is, written out to the recording device 140 or the recording medium of the recording device 140. When writing out at least a part of the recording information, the control section 13 controls the recording section 11 and the writing-out section 34 such that at least a part of the recording information is recorded in the recording device 140 or on the recording medium of the recording device 140. In FIGS. 1 and 2, the recording information written out to the recording device 140 is denoted by the symbol S5.

(Configuration of Display Apparatus)

Next, description will be made on the configuration of the display apparatus 2, with reference to FIG. 3. FIG. 3 is a functional block diagram showing the configuration of the display apparatus 2. The display apparatus 2 includes a display section 40 for displaying the plurality of output videos. The display section 40 is configured by a liquid crystal panel, for example. In the present embodiment, the plurality of output videos are the output videos S1 to S3.

The display apparatus 2 further includes three video input sections 41, 42, 43, three signal detection sections 44, 45, 46, a display signal switching section 47, a display signal adjusting section 48, a communication section 49, a storage section 50, a control section 51, and an operation section 52.

Each of the video input sections 41 to 43 includes an input terminal that receives an input of the output video. Examples of the terminals used as the input terminals include an SDI terminal, a Y/C terminal, and the like. The video input section 41 receives an input of the output video S1a outputted from the video output section 30 (see FIG. 2). The video input section 42 receives an input of the output video S2a outputted from the video output section 31 (see FIG. 2). The video input section 43 receives an input of the output video S3a outputted from the video output section 32 (see FIG. 2).

The signal detection section 44 detects presence or absence of the output video S1a in the video input section 41, and outputs the output video S1a inputted to the video input section 41 to the display signal switching section 47. The signal detection section 45 detects presence or absence of the output video S2a in the video input section 42, and outputs the output video S2a inputted to the video input section 42 to the display signal switching section 47. The signal detection section 46 detects presence or absence of the output video S3a in the video input section 43, and outputs the output video S3a inputted to the video input section 43 to the display signal switching section 47.

The operation section 52 includes a plurality of switches for setting an input source of each of the output videos in the display apparatus 2, setting correction parameters for the output videos S1 to S3 in the display apparatus 2, and setting the display styles of the output videos S1 to S3 in the display apparatus 2. In the setting of the input source of each of the output videos, one or more video input sections can be selected as the input source. One or more output videos, which are inputted to the one or more video input sections selected by the operation section 52, are displayed on the display section 40.

The correction parameters are parameters used for correcting the output video when the output video is displayed on the display section 40. Examples of the correction parameters include gamma values used for gamma correction, contrast, brightness, color temperature, and the like. These parameters are set for each of the video output apparatuses, for example.

The setting of the display styles is, specifically, a setting of an enlarged display of the entirety or a cut-out part of the output video that is displayed on the display section 40 (so-called scan mode setting) and a setting of a combining method of a plurality of output videos in the case where a plurality of video input sections are selected as input sources. Examples of the combining method include a picture-out-picture (POP) method in which a plurality of output videos are simultaneously displayed side by side, a picture-in-picture (PIP) method in which two output videos are simultaneously displayed in a main screen and in a sub-screen, respectively.

The correction parameters are set in advance by the operation section 52 or other input means before the surgery using the endoscopic surgical system 100. The storage section 50 stores the information on the correction parameters set in advance. If the correction parameters are changed by the operation section 52 during the surgery using the endoscopic surgical system 100, the correction parameters stored in the storage section 50 may be updated with the changed correction parameters.

The communication section 49 is configured to be controlled by the control section 51, and to transmit and receive predetermined information to and from the image recording apparatus 1. The predetermined information includes the above-described display state information. More specifically, the communication section 49 transmits, to the communication section 33 of the image recording apparatus 1, the information on the input source and the information on the display style that are set by the operation section 52 and the information on the correction parameters stored in the storage section 50. When causing the plurality of output videos, which are included in the recording information retained in the recording section 11 of the image recording apparatus 1, to be displayed on the display apparatus 2, the communication section 33 of the image recording apparatus 1 outputs the display state information included in the recording information to the display apparatus 2. In this case, the communication section 49 outputs the received display state information to the control section 51.

The display signal switching section 47 is configured to be controlled by the control section 51, and to select any of the inputted output videos S1a to S3a and output the selected output video to the display signal adjusting section 48. The display signal switching section 47 outputs, to the display signal adjusting section 48, one or more output videos inputted to the one or more video input sections selected as input sources by the operation section 52, or one or more output videos inputted to the one or more video input sections selected based on the information on the input sources included in the recording information transmitted from the image recording apparatus 1.

The display signal adjusting section 48 is configured to be controlled by the control section 51, and to perform predetermined adjustment on the inputted one or more output videos and output the adjusted one or more output videos to the display section 40. The display section 40 displays the one or more output videos adjusted by the display signal adjusting section 48. The display signal adjusting section 48 adjusts the one or more output videos according to the setting of the display style performed by the operation section 52 or the setting of the display style included in the recording information transmitted from the image recording apparatus 1. In addition, the display signal adjusting section 48 adjusts the one or more output videos according to the correction parameters stored in the storage section 50 or the correction parameters included in the recording information transmitted from the image recording apparatus 1.

Figure 4:
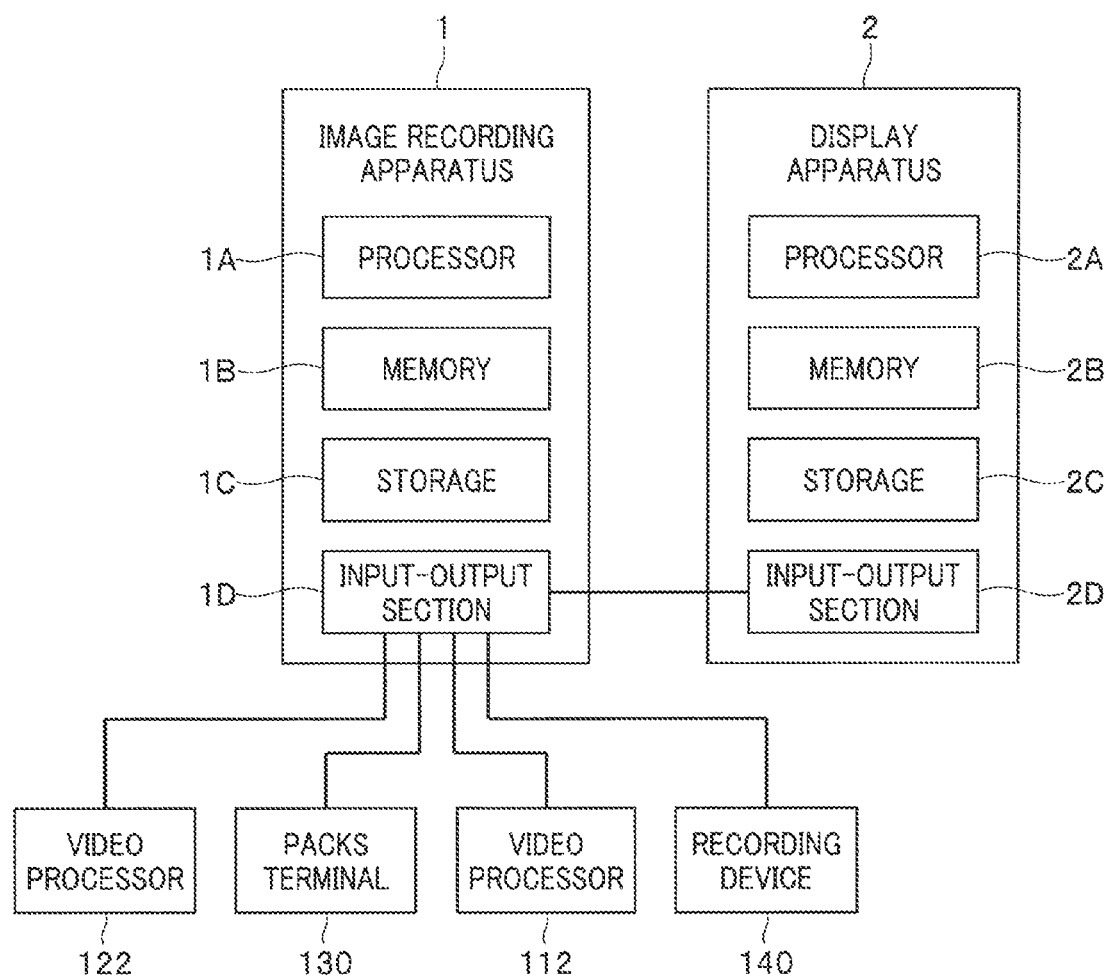
FIG. 4 is a functional block diagram showing an example of hardware configurations of the image recording apparatus and the display apparatus according to the embodiment of the present invention.

Now, description will be made on the hardware configurations of the image recording apparatus 1 and the display apparatus 2 with reference to FIG. 4. FIG. 4 is an explanatory diagram showing an example of the hardware configurations of the image recording apparatus 1 and the display apparatus 2. In the example shown in FIG. 4, the image recording apparatus 1 is provided with a processor 1A, a memory 1B, a storage 1C, an input-output section 1D constituted of an input-output interface. The display apparatus 2 is provided with a processor 2A, a memory 2B, a storage 2C, and an input-output section 2D constituted of an input-output interface. The processor 1A is used for executing the functions at least some of the plurality of constituent elements, such as the control section 13 and the encoding section 28, of the image recording apparatus 1. The processor 2A is used for executing the functions of at least some of the plurality of constituent elements, such as the display signal adjusting section 48 and the control section 51, of the display apparatus 2. Each of the processors 1A and 2A is configured of an FPGA (Field Programmable Gate Array), for example. At least some of the plurality of constituent elements of the image recording apparatus 1 and at least some of the plurality of constituent elements of the display apparatus 2 may be configured respectively as circuit blocks in the FPGA.

Each of the memories 1B and 2B is configured by a rewritable volatile storage element such as RAM. Each of the storages 1C and 2C is configured by a rewritable non-volatile storage apparatus such as a flash memory or a hard disk apparatus. The memory 1B and the storage 1C are used for executing the functions of the recording section 11 and the storage section 12 of the image recording apparatus 1. The memory 2B and the storage 2C are used for executing the function of the storage section 50 of the display apparatus 2.

The input-output section 1D is used for transmitting and receiving signals between the image recording apparatus 1 and an outside. In the present embodiment, the input-output section 1D includes the video input sections 21 to 23, the video output sections 30 to 32, the communication section 33, and the writing-out section 34. The input-output section 2D is used for transmitting and receiving signals between the display apparatus 2 and an outside. In the present embodiment, the input-output section 2D includes the video input sections 41 to 43 and the communication section 49.

Each of the processors 1A and 2A may be configured by a central processing unit (hereinafter referred to as CPU). In this case, the functions of at least some of the plurality of constituent elements of the image recording apparatus 1 may be implemented by the CPU reading a program from the storage 1C and executing the program. Similarly, the functions of at least some of the plurality of constituent elements of the display apparatus 2 may be implemented by the CPU reading a program from the storage 2C and executing the program.

The hardware configurations of the image recording apparatus 1 and the display apparatus 2 are not limited to the example shown in FIG. 4. For example, the plurality of constituent elements of the image recording apparatus 1 may be configured as separate electronic circuits. Similarly, the plurality of constituent elements of the display apparatus 2 may be configured as separate electronic circuits.

(Operation at the Time of Recording Information Generation)

Next, among the operations of the image recording apparatus 1, the operation at the time of recording information generation will be described. Here, description will be made on the operation at the time of recording information generation supposing that a surgery is performed according to the first to fifth steps shown below. The first step is a step of causing the output video S2, which is an MRI image stored in the medical image management system, to be displayed on the display apparatus 2 in order to confirm a target site for the surgery before the start of the surgery. The second step is a step of causing the output video S1, which is from the first endoscope 110 as a surgical endoscope, to be displayed on the display apparatus 2, after the start of the surgery. The third step is a step of causing the output video S2, which is the MRI image, to be displayed again on the display apparatus 2, immediately before resection of the target site. The fourth step is a step of causing the output video S3, which is from the second endoscope 120 as a gastrointestinal endoscope, to be displayed on the display apparatus 2, in order to confirm a leak after anastomosis. The fifth step is a step of causing the output video S1 from the first endoscope 110 and the output video S3 from the second endoscope 120 to be displayed on the display apparatus 2, for final confirmation. The procedure is terminated at the timing of the end of the fifth step, and the recording of the output videos S1 to S3 is terminated.

Hereinafter, the timing at which the output video S2 is displayed in the first step is denoted by the symbol Ta, the timing at which the output video S1 is displayed in the second step is denoted by the symbol Tb, the timing at which the output video S2 is displayed in the third step is denoted by the symbol Tc, the timing at which the output video S3 is displayed in the fourth step is denoted by the symbol Td, the timing at which the output videos S1, S3 are displayed in the fifth step is denoted by the symbol Te, and the timing at which the recording of the output videos S1 to S3 is terminated is denoted by the symbol Tf.

Figure 5:
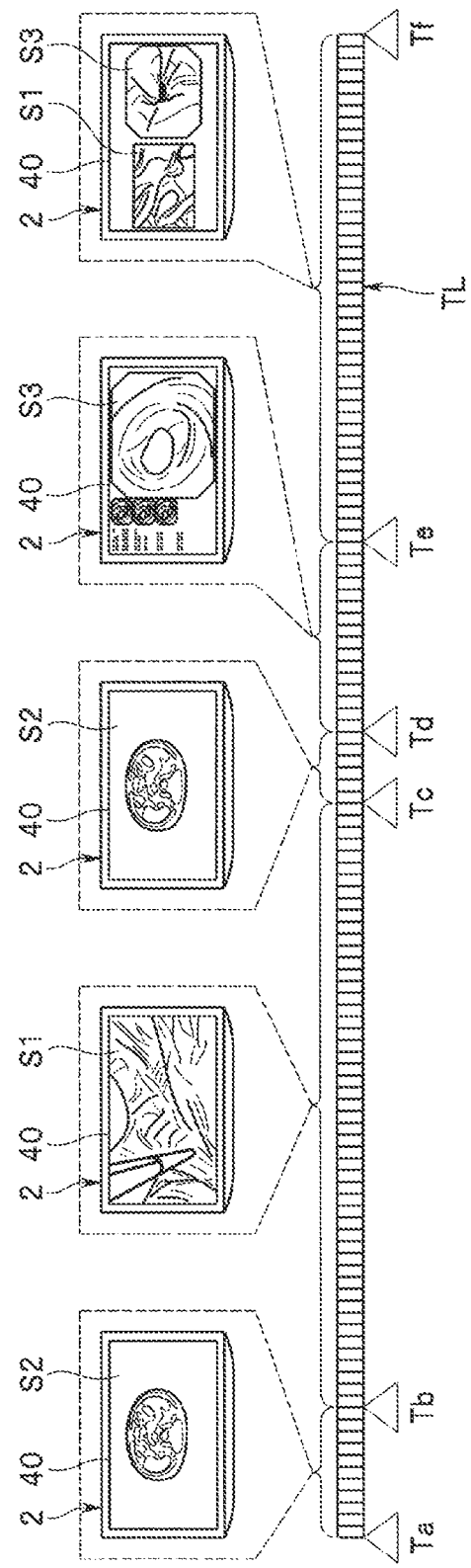
FIG. 5 is an explanatory view showing output videos that are displayed on a display section of the display apparatus in the embodiment of the present invention.

FIG. 5 is an explanatory view showing the output videos (hereinafter, also referred to as display videos) that are displayed on the display section 40 of the display apparatus 2 when the surgery is performed according to the first to fifth steps. In FIG. 5, the rectangular figure long in one direction, to which the symbol TL is added, indicates the timeline TL schematically showing the temporal positions of the display videos. The triangles to which the symbols Ta, Tb, Tc, Td, Te, and Tf are added respectively represent the temporal positions of the timings Ta, Tb, Tc, Td, Te, and Tf in the timeline TL. As shown in FIG. 5, the output video S2 is displayed between the timing Ta and the timing Tb, the output video S1 is displayed between the timing Tb and the timing Tc, the output video S2 is displayed between the timing Tc and the timing Td, the output video S3 is displayed between the timing Td and the timing Te, and the output videos S1, S3 are displayed between the timing Te and the timing Tf.

The control section 13 controls the output signal switching section 29 such that the output videos S1 to S3 inputted to the video input sections 21 to 23 are outputted to the display apparatus 2 in a period from the timing Ta to the timing Tf. Further, the control section 13 controls the recording section 11, the storage section 12, and the input signal switching section 27, so as to generate the recording information by associating the data of the output videos S1 to S3 with the display state information outputted from the display apparatus 2 in a period from the timing Ta to the timing Tf.

In the present embodiment, the display state information includes identification information for identifying, among the plurality of output videos, the output video that is displayed on the display apparatus 2. The control section 13 controls the recording section 11 and the storage section 12, so as to identify at least one timing at which the contents of the identification information change, and impart at least one editing point indicating the at least one timing to data of at least one output video corresponding to the changed contents of the identification information, among the data of the plurality of output videos.

In addition, the control section 13 controls the recording section 11 and the storage section 12, so as to impart an editing point, which indicates a start of the recording of the plurality of output videos, to the data of at least one output video displayed on the display section 40 of the display apparatus 2 at the timing immediately after the start of the recording of the plurality of output videos, and impart an editing point, which indicates an end of the recording of the plurality of output videos, to the data of at least one output video displayed on the display section 40 of the display apparatus 2 at the timing immediately before the end of the recording of the plurality of output videos.

Furthermore, as described above, in the present embodiment, the recording section 11 generates the recording information in association with the time information, and the storage section 12 stores the display state information in association with the time information. The control section 13 controls the recording section 11 and the storage section 12, so as to impart the editing points based on the time information.

Figure 6:
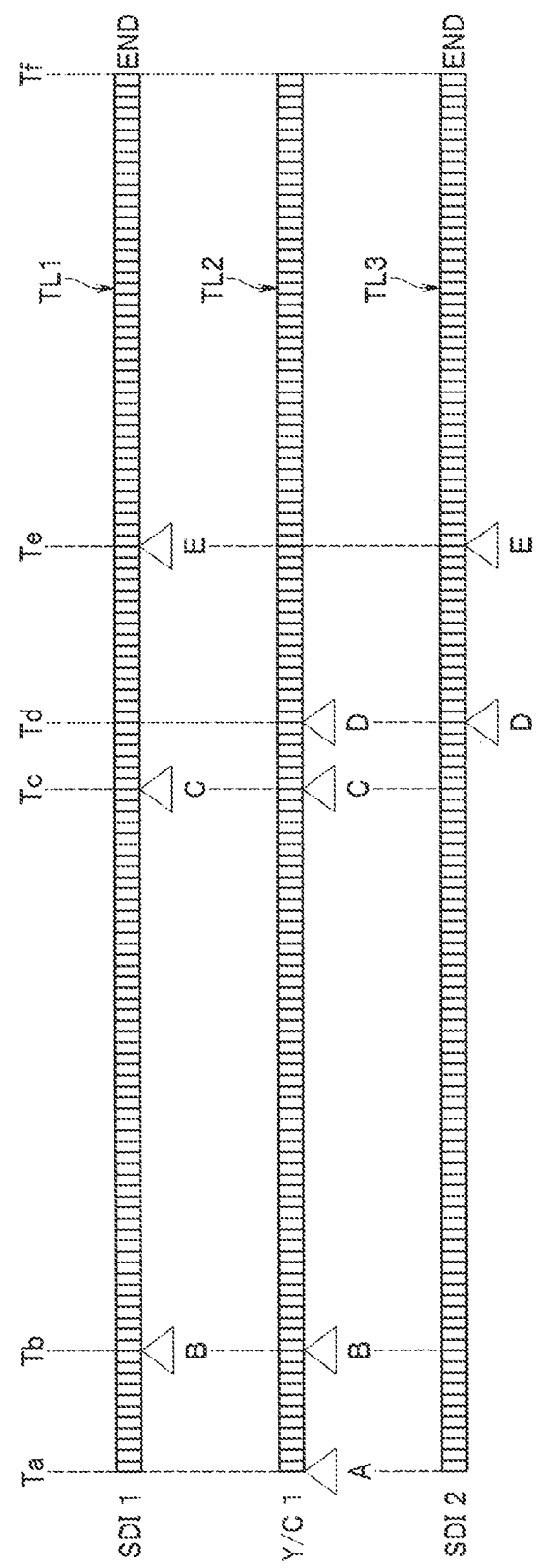
FIG. 6 is an explanatory view for explaining editing points imparted to data of a plurality of output videos in the embodiment of the present invention.

FIG. 6 is an explanatory view for explaining the editing points to be imparted to the data of the output videos S1 to S3 when the surgery is performed according to the above-described first to fifth steps. In FIG. 6, the rectangular figure long in one direction, to which the symbol TL1 is added, indicates the timeline TL1 schematically showing the temporal positions of the video inputted to the video input section 41 of the display apparatus 2, the rectangular figure long in one direction, to which the symbol TL2 is added, indicates the timeline TL2 schematically showing the temporal positions of the video inputted to the video input section 42 of the display apparatus 2, and the rectangular figure long in one direction, to which the symbol TL3 is added, indicates the timeline TL3 schematically showing the temporal positions of the video inputted to the video input section 43 of the display apparatus 2. In FIG. 6, on the left side of the respective timelines TL1 to TL3, the names of the input terminals of the video input sections 41 to 43 are shown. In FIG. 6, the symbol "SDI 1" represents the input terminal of the video input section 41, the symbol "Y/C 1" represents the input terminal of the video input section 42, and the symbol "SDI 2" represents the input terminal of the video input section 43. Furthermore, in FIG. 6, the temporal positions of the editing points are shown by the triangles.

In the present embodiment, the video inputted to the video input section 41 is the output video S1, the video inputted to the video input section 42 is the output video S2, and the video inputted to the video input section 43 is the output video S3. Therefore, substantially, the timeline TL1 indicates the temporal positions of the output video S1, the timeline TL2 indicates the temporal positions of the output video S2, and the timeline TL3 indicates the temporal positions of the output video S3.

The timing Ta is also the timing at which the recording of the output videos S1 to S3 is started. The output video S2 is the output video that is displayed on the display section 40 of the display apparatus 2 at the timing immediately after the start of the recording of the output videos S1 to S3. In this case, an editing point "Index A" indicating the timing Ta is imparted to the data of the output video S2. Note that FIG. 6 shows "Index A" simply as "A".

If the surgery is performed according to the above-described first to fifth steps, the identification information changes at each of the timings Tb to Te. At the timing Tb, the contents of the identification information corresponding to the output videos S1, S2 change. In this case, "Index B" is imparted, as the editing point indicating the timing Tb, to the data of the output videos S1, S2. Note that FIG. 6 shows "Index B" simply as "B".

At the timing Tc, the contents of the identification information corresponding to the output videos S1, S2 change. In this case, "Index C" is imparted, as the editing point indicating the timing Tc, to the data of the output videos S1, S2. Note that FIG. 6 shows "Index C" simply as "C".

At the timing Td, the contents of the identification information corresponding to the output videos S2, S3 change. In this case, "Index D" is imparted, as the editing point indicating the timing Td, to the data of the output videos S2, S3. Note that FIG. 6 shows "Index D" simply as "D".

At the timing Te, the contents of the identification information corresponding to the output videos S1, S3 change. In this case, "Index E" is imparted, as the editing point indicating the timing Te, to the data of the output videos S1, S3. Note that FIG. 6 shows "Index E" simply as "E".

The timing Tf is the timing at which the recording of the output videos S1 to S3 is terminated. The output videos S1 and S3 are the output videos that are displayed on the display section 40 of the display apparatus 2 at the timing immediately before the end of the recording of the output videos S1 to S3. In this case, "END" is imparted, as the editing point indicating the timing Tf, to the data of the output videos S1 and S3.

Here, description will be made on an example of the display state information with reference to FIG. 7. FIG. 7 is a chart showing the example of display state information. FIG. 7 shows the five editing points, "Index A", "Index B", "Index C", "Index D", and Index E", and shows, as the output videos corresponding to the five editing points, the output videos that are displayed on the display section 40 of the display apparatus 2 immediately after the timings corresponding to the respective editing points. In addition, FIG. 7 shows, as the time corresponding to each of the five editing points, the elapsed time from the clock time at which the recording of the output videos S1 to S3 was started to each of the timings corresponding to each of the editing points.

FIG. 7 also shows the names of the input terminals of the video input sections 41 to 43 of the display apparatus 2, as the information on the input sources of the output videos corresponding to the five editing points.

FIG. 7 also shows the respective setting values of the gamma values (shown just as "GAMMA" in FIG. 7), the contrast, the brightness, and the color temperature, as the correction parameters for the output videos corresponding to the five editing points. Note that the setting value peculiar to each of the video output apparatuses is used as the gamma value. Therefore, FIG. 7 shows the character strings indicating the corresponding video output apparatuses, instead of displaying the respective setting values of the gamma values. In FIG. 7, "Endoscope 1", "Endoscope 2", and "DICOM" are the character strings indicating the settings of the gamma values.

FIG. 7 also shows, as the information on the display styles of the output videos corresponding to the five editing points, the scan mode setting and the setting of the combining method of the plurality of output videos. In the scan mode setting, "OFF" indicates that enlargement and the like of the output videos are not performed, and "2" indicates that enlargement and the like of the output video are performed with a predetermined method. In addition, here, the case where one or two video input sections can be selected as an input source is supposed. In FIG. 7, "two-screen display" indicates the setting of the combining method. In the setting of "two-screen display", "OFF" indicates the case where one video input section is selected as the input source and combining of a plurality of output videos is not performed, while "POP" indicates that two output videos are displayed in the picture-out-picture (POP) method.

In the present embodiment, the gamma values are used as the plurality of pieces of setting value information for identifying the plurality of video output apparatuses. The storage section 12 includes the table showing the correspondence between the plurality of video output apparatuses and the plurality of pieces of setting value information. For example, the table shows that "Endoscope 1" corresponds to the first endoscope 110, "Endoscope 2" corresponds to the second endoscope 120, and "DICOM" corresponds to the PACS terminal 130. The control section 13 uses the table to identify that the output source of the output video S1 is the first endoscope 110, the output source of the output video S2 is the PACS terminal 130, and the output source of the output video S3 is the second endoscope 120. FIG. 7 shows the output source (shown as "VIDEO INPUT APPARATUS" in FIG. 7) of the output video corresponding to each of the five editing points identified by the control section 13. Note that, in FIG. 7, "PACS" indicates the PACS terminal 130, "SURGICAL ENDOSCOPE" indicates the first endoscope 110, and "GASTROINTESTINAL ENDOSCOPE" indicates the second endoscope 120.

In addition, at least one of the information on the input sources and the information on the gamma values, in the present embodiment, at least the information on the input sources is used as the identification information. In other words, in the present embodiment, at least one of the timing at which the input source is changed and the timing at which the gamma value is changed, here, at least the timing at which the input source is changed is regarded as the timing at which the contents of the identification information change, and an editing point is imparted. Hereinafter, description will be made on the relation between the input sources and the editing points, with reference to FIG. 6 and FIG. 7. The description below also includes the description on the information on the output source added to the data of each of the output videos S1 to S3.

At the timing Tb, the input source is changed from "Y/C 1" (input terminal of the video input section 42) to "SDI 1" (input terminal of the video input section 41). In this case, "Index B" is imparted, as the editing point, to the data of the output video S2 corresponding to "Y/C 1" and the data of the output video S1 corresponding to "SDI 1". At the timing Ta, the gamma value is set to "DICOM", and at the timing Tb, the gamma value is changed from "DICOM" to "Endoscope 1". In this case, "PACS" (PACS terminal 130) corresponding to "DICOM" is added, as the information on the output source, to the data of the output video S2 in the period from the timing Ta to the timing Tb.

At the timing Tc, the input source is changed from "SDI 1" to "Y/C 1". In this case, "Index C" is imparted, as the editing point, to the data of the output videos S1, S2. In addition, at the timing Tc, the gamma value is changed from "Endoscope 1" to "DICOM". In this case, "surgical endoscope" (first endoscope 110) corresponding to "Endoscope 1" is added, as the information on the output source, to the data of the output video S1 in the period from the timing Tb to the timing Tc.

Furthermore, at the timing Td, the input source is changed from "Y/C 1" to "SDI 2" (the input terminal of the video input section 43). In this case, "Index D" is imparted, as the editing point, to the data of the output video S2 and the data of the output video S3 corresponding to "SDI 2". At the timing Td, the gamma value is changed from "DICOM" to "Endoscope 2". In this case, "PACS" (PACS terminal 130) corresponding to "DICOM" is added, as the information on the output source, to the data of the output video S2 in the period from the timing Tc to the timing Td.

At the timing Te, the input source is changed from "SDI 2" to "SDI 1" and "SDI 2". In this case, "Index E" is imparted, as the editing point, to the data of the output videos S1 and S3. Furthermore, at the timing Te, the gamma value is changed from "Endoscope 2" to "Endoscope 1, Endoscope 2", and at the timing Tf, the recording of the output videos S1 to S3 is terminated. In this case, "gastrointestinal endoscope" (second endoscope 120) corresponding to "Endoscope 2" is added, as the information on the output source, to the data of the output video S3 in the period from the timing Td to the timing Te and the data of the output video S3 in the period from the timing Te to the timing Tf, and "surgical endoscope" (first endoscope 110) corresponding to "Endoscope 1" is added, as the information on the output source, to the data of output video S1 in the period from the timing Te to the timing Tf.

So far, description has been made on the case where the timing at which the input source is changed is regarded as the timing at which the contents of the identification information change. Note that, as described in the modification to be described later, there is a case where the input source is not changed, but the gamma value is changed. In such a case, the timing at which the gamma value is changed is regarded as the timing at which the contents of the identification information change, and the editing point indicating the timing at which the gamma value is changed is imparted to the data of the output video.

(Operation at the Time of Editing Screen Display)

Figure 8:
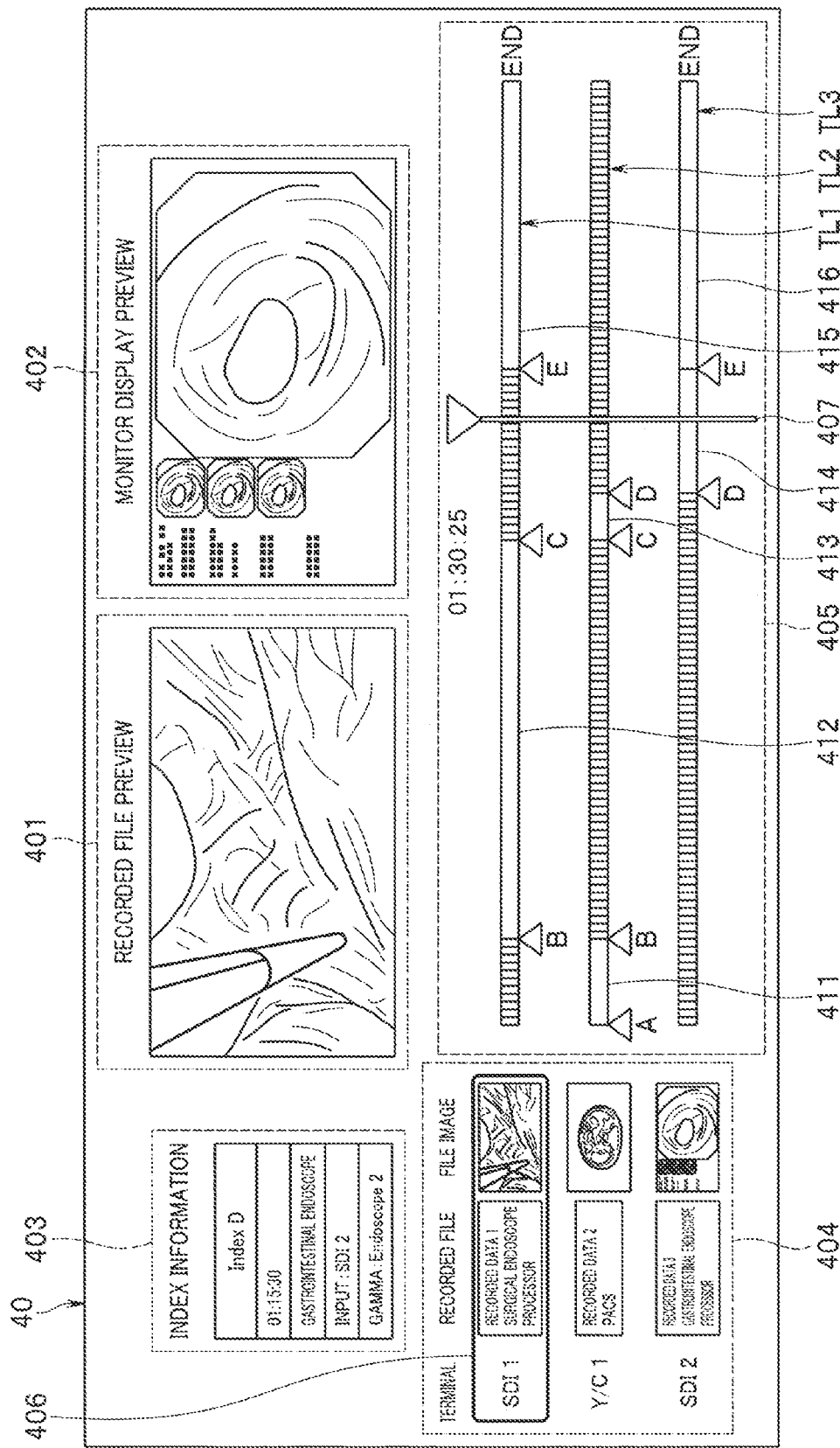
FIG. 8 is an explanatory view showing an example of an editing screen displayed on the display section of the display apparatus in the embodiment of the present invention.

Next, among the operations of the image recording apparatus 1, the operation for causing the screen for editing (hereinafter, referred to as editing screen) to be displayed on the display apparatus 2 will be described with reference to FIG. 8. The editing screen is for editing the recording information retained in the recording section 11. FIG. 8 is an explanatory view showing an example of the editing screen displayed on the display section 40 of the display apparatus 2. In the example shown in FIG. 8, the editing screen includes a first region 401, a second region 402, a third region 403, a fourth region 404, and a fifth region 405. In the first and second regions 401, 402, the display images corresponding to the output videos are displayed. In the third region 403, the information on the editing point is displayed. In the fourth region 404, pieces of information on the output videos are displayed. In the fifth region 405, the timelines of the output videos are displayed.

FIG. 8 shows the editing screen in the case of editing the recording information including the data of the output videos S1 to S3 to each of which the editing points are imparted in the manner as described with reference to FIGS. 6 and 7, and to each of which the information on the output source is added in the manner as described with reference to FIGS. 6 and 7. Note that, in FIG. 8, the output video S1 is indicated as recorded data 1, the output video S2 as recorded data 2, and the output video S3 as recorded data 3. In the example shown in FIG. 8, in the fourth region 404, the names of the input terminals of the video input sections 41 to 43 of the display apparatus 2, which correspond respectively to the output videos S1 to S3, the names of the video output apparatuses corresponding respectively to the output videos S1 to S3, and images indicating the contents of the output videos S1 to S3 are displayed. Each of the images may be a still image located at the temporal head of each of the output videos, for example.

In the fourth region 404, a frame 406 is further displayed, as selecting means with which one of the output videos S1 to S3 is selected. The frame 406 is the selecting means that can be operated by the operation section 52 of the display apparatus 2 or other operation means. FIG. 8 shows an example in which the output video S1 is selected with the frame 406.

In the first region 401, among the output videos S1 to S3, the output video selected with the frame 406 is displayed as a display image. In the example shown in FIG. 8, the output video S1 is displayed in the first region 401. The display image may be a moving image or a still image.

In the fifth region 405, the timelines TL1 to TL3 indicating the temporal positions of the videos inputted to the video input sections 41 to 43, the markers indicating the editing points, and the markers each indicating a time range during which each of the output videos was being displayed on the display section 40 of the display apparatus 2 at the time of the recording information generation are displayed. In FIG. 8, the editing points "Index A", "Index B", "Index C", "Index D", and "Index E" are shown respectively by the triangular markers to which the symbols A, B, C, D, and E are added, respectively. The white blank parts 411, 412, 413, 414, 415, and 416 in the timelines TL1 to TL3 are the markers each indicating the above-described time range.

In the fifth region 405, a seek bar 407 as predetermined indicator means is further displayed. The seek bar 407 is displayed so as to overlap the timelines TL1 to TL3. The seek bar 407 is the indicator means that can be operated by the operation section 52 of the display apparatus 2 or other operation means. With the seek bar 407, any temporal position on the timelines TL1 to TL3 can be selected. The time displayed near the seek bar 407 represents the temporal position selected by the seek bar 407.

As described above, substantially, the timeline TL1 indicates the temporal positions of the output video S1, the timeline TL2 indicates the temporal positions of the output video S2, and the timeline TL3 indicates the temporal positions of the output video S3. Therefore, it can be said that the timelines TL1 to TL3 substantially indicating the temporal positions of the output videos S1 to S3 are displayed in the fifth region 405.

In the second region 402, among the output videos S1 to S3, the output video, which was being displayed on the display section 40 of the display apparatus 2 at the timing corresponding to the temporal position selected by the seek bar 407, is displayed as a display image. In other words, the seek bar 407 is means that selects any temporal position on the timelines TL1 to TL3 and selects the output video which was being displayed on the display section 40 of the display apparatus 2 at the timing corresponding to the selected temporal position. In the example shown in FIG. 8, the output video S3 is displayed in the second region 402. The display image may be a moving image or a still image.

In the third region 403, the name of the editing point immediately before the temporal position selected by the seek bar 407 and the information on the output video which was being displayed on the display section 40 of the display apparatus 2 at the timing corresponding to the temporal position selected by the seek bar 407 are displayed. In the example shown in FIG. 8, "Index D" is displayed as the name of the editing point. In addition, in FIG. 8, as the information on the output video, the name of the video output apparatus corresponding to the output video, the name of the input terminal of the video input section corresponding to the output video, and the character string indicating the setting of the gamma value corresponding to the output video are displayed. In addition, as shown in FIG. 8, the time indicating the temporal position of the editing point is further displayed in the third region 403.

In order to provide the editing screen shown in FIG. 8, the control section 13 causes the recording section 11 to output at least a part of the recording information to the display apparatus 2 such that the display image, the editing points, and at least a part of the display state information are displayed on the display section 40 of the display apparatus 2. The display image corresponds to at least one output video selected, from among the output videos S1 to S3 recorded in the recording section 11, by the seek bar 407 as the predetermined indicator means. The control section 51 of the display apparatus 2 causes the display section 40 to display the display image, the editing point, and at least a part of the display state information, based on the recording information.

In addition, the control section 13 causes the recording section 11 to output the data of the output videos S1 to S3 to the display apparatus 2 such that the timelines TL1 to TL3, the triangular markers, and the white blank parts are displayed on the display section 40 of the display apparatus 2. The timelines TL1 to Tl3 substantially indicate the temporal positions of the output videos S1 to S3. Each of the triangular markers is a first type of marker that indicates the editing point. Each of the white blank parts is a second type of marker that indicates the time range during which each of the output videos was being displayed on the display section 40 of the display apparatus 2 at the time of the recording information generation. The control section 51 of the display apparatus 2 causes the display section 40 to display the timelines TL1 to TL3, the triangular markers, and the white blank parts, based on the data of the output videos S1 to S3.

Note that the first type of marker is not limited to the triangles, but any display means such as arrows, dots, or a characters can be used. Similarly, the second type of marker is not limited to the white blanks, but any display means such as arrows, coloring, hatching, and the like can be used.

In the recording information, the output videos S1 to S3 themselves are outputted to the display apparatus 2 via the output signal switching section 29 and the video output sections 30 to 32. Furthermore, among the data of the output videos S1 to S3, the display state information, information on the editing points, and the information on the output sources are outputted to the display apparatus 2 via the control section 13 and the communication section 33.

(Other Operations)

Next, other operations of the image recording apparatus 1 will be described. As described above, the control section 13 of the image recording apparatus 1 is capable of causing the plurality of output videos included in the recording information retained in the recording section 11 to be displayed on the display apparatus 2. In the present embodiment, the control section 13 causes the recording section 11 to output at least a part of the recording information to the display apparatus 2 such that the output videos S1 to S3 are displayed on the display section 40 of the display apparatus 2 in the display state which is the same as at least a part of the display state at the time of the recording information generation. In other words, the control section 13 causes the recording section 11 to output at least a part of the recording information to the display apparatus 2 such that a preview video, in which each of the output videos S1 to S3 is displayed in the same manner as was being displayed on the display section 40 of the display apparatus 2 at the time of the recording information generation, is reproduced on the display section 40 of the display apparatus 2. The control section 51 of the display apparatus 2 reproduces the preview video based on the recording information.

Here, description will be made on the above-described preview video by taking, as an example, the case where the editing points are imparted to the output videos S1 to S3 in the manner as described above with reference to FIG. 6 and FIG. 7. In the preview video, first, the output video S2 between "Index A" and "Index B" is displayed. Next, the output video S1 between "Index B" and "Index C" is reproduced. Next, the output video S2 between "Index C" and "Index D" is reproduced. Next, the output video S3 between "Index D" and "Index E" is reproduced. Next, the output videos S1, S3 between "Index E" and "END" are reproduced.

The control section 51 of the display apparatus 2 reconstructs the display state at the time of the recording information generation, by using the display state information included in the recording information, more specifically, the information on the input source, the information on the correction parameters, and the information on the display style. In particular, even in the case where a plurality of output videos are displayed, as in the period between "Index E" and "END", the control section 51 reconstructs the state where the plurality of output videos are displayed based on the information on the display style. The preview video may be the one in which the display state at the time of the recording information generation is fully reconstructed, or may be the one in which the image quality, the reproducing speed, and the like are different from those in the display state at the time of the recording information generation.

In addition, the image recording apparatus 1 is capable of generating a recording video similar to the above-described preview video. In the present embodiment, the control section 13 controls at least one of the recording section 11 and the storage section 12, here, at least the recording section 11 so as to generate a recording video corresponding to the video displayed on the display section 40 of the display apparatus 2 at the time of the recording information generation, by using the output videos S1 to S3 and at least a part of the display state information. Generation of the recording video may be performed simultaneously with the recording information generation, i.e., in real time, or may be performed after the recording information generation. In the latter case, the recording video is generated based on the recording information retained in the recording section 11. The generated recording video is retained by the recording section 11.

The recording video can be recorded, that is, written out to the recording device 140 or the recording medium of the recording device 140. When writing out the recording video, the control section 13 controls the recording section 11 and the writing-out section 34 such that the recording video retained in the recording section 11 is recorded in the recording device 140 or on the recording medium of the recording device 140.

(Working and Effects)

Next, description will be made on the working and effects of the image recording apparatus 1 according to the present embodiment. In the present embodiment, the recording information is generated by associating the data of the output videos S1 to S3 with the display state information. In the present embodiment, in particular, the display state information includes the identification information for identifying, among the output videos S1 to S3, the output video that is displayed on the display section 40 of the display apparatus 2. With such a configuration, the present embodiment is capable of identifying the part, which was being displayed on the display section 40 of the display apparatus 2, in each of the recorded output videos S1 to S3. Thus, the present embodiment is capable of improving the efficiency of the editing operations of the output videos S1 to S3.

In addition, in the present embodiment, the timing at which the contents of the identification information change is identified, and the editing point indicating the timing at which the contents of the identification information change is added to each of the data of the output videos S1 to S3. According to the present embodiment, detection of the timings of the switching among the output videos S1 to S3 becomes easy by using the editing points. As a result, it is possible to use the recording information effectively.

In addition, in the present embodiment, the display state information includes, as the setting value information, the information on the gamma values for identifying the first endoscope 110, the second endoscope 120, and the PACS terminal 130, and the storage section 12 stores the table showing the correspondence between the information on the gamma values and the first endoscope 110, the second endoscope 120, and the PACS terminal 130. In the present embodiment, the output sources of the output videos S1 to S3 are identified by using the table, and the information on the identified output source is added to each of the data of the output videos S1 to S3. With such a configuration, the present embodiment enables the effective use of the recording information.

In addition, in the present embodiment, the recording information is generated by associating the data of the output videos S1 to S3 with the display state information, to thereby enable the output videos S1 to S3 to be displayed on the display apparatus 2 or another display apparatus, while reconstructing the display state at the time of the recording information generation on the display apparatus 2 or the other display apparatus.

In addition, in the present embodiment, the editing screen can be displayed on the display section 40 of the display apparatus 2. The editing screen includes the timelines TL1 to TL3 substantially indicating the temporal positions of the output videos S1 to S3, the markers (triangles, for example) indicating the editing points, and the markers (white blanks, for example) indicating the time range during which each of the output videos was being displayed on the display section 40 of the display apparatus 2 at the time of the recording information generation. With such a configuration, the present embodiment enables a user to visually recognize the timing of switching among the output videos S1 to S3 on the display apparatus 2 and the timing in which each of the output videos S1 to S3 was being displayed on the display apparatus 2.

As described above, the present embodiment is capable of generating the recording video corresponding to the video displayed on the display section 40 of the display apparatus 2 at the time of the recording information generation. The recording video has a file size smaller than that of the recording information including all the data of the output videos S1 to S3. Accordingly, using the recording video instead of the recording information can reduce the used capacity of the storage 1C of the image recording apparatus 1 and the used capacity of the recording device 140 or the recording medium of the recording device 140.

(Modification)

Next, description will be made on the modification of the present embodiment. The modification assumes a case where the surgery is performed according to the following sixth and seventh steps, in addition to the above-described first to fifth steps. The sixth step is the step of replacing the first endoscope 110 with the second endoscope 120 such that the output video S3 from the second endoscope 120 is inputted to the video input section 21 of the image recording apparatus 1 after the above-described second step, to cause the output video S3 to be displayed on the display apparatus 2. In the sixth step, in particular, the output video S3 inputted to the video input section 21 is inputted to the video input section 41 of the display apparatus 2 via the signal detection section 24, the output signal switching section 29, and the video output section 30. In other words, the sixth step is a step of replacing the first endoscope 110 with the second endoscope 120 such that the output video S3 is inputted to the video input section 41 to which the output video S1 has been inputted in the second step.

The seventh step is a step of replacing the second endoscope 120 with the first endoscope 110 again such that the output video S1 from the first endoscope 110 is inputted to the video input section 21, to cause the output video S1 to be displayed on the display apparatus 2. In other words, the seventh step is a step of replacing the second endoscope 120 with the first endoscope 110 such that the output video S1 is inputted to the video input section 41 to which the output video S3 has been inputted in the sixth step. The above-described third step is performed after the seventh step.

Hereinafter, the timing at which the output video S3 is displayed in the sixth step is denoted by the symbol Tb1, and the timing at which the output video S1 is displayed in the seventh step is denoted by the symbol Tb2. In the modification, in particular, the output video S1 is displayed on the display section 40 of the display apparatus 2 between the timing Tb and the timing Tb1. The output video S3 is displayed on the display section 40 of the display apparatus 2 between the timing Tb1 and the timing Tb2. The output video S1 is displayed on the display section 40 of the display apparatus 2 between the timing Tb2 and the timing Tc.

FIG. 9 is an explanatory view for explaining the editing points imparted to each of the data of the output videos S1 to S3 in the case where the surgery is performed according to the above-described first to fifth steps and the sixth and seventh steps. FIG. 9 shows the timeline TL1 schematically showing the temporal positions of the video inputted to the video input section 41, the timeline TL2 schematically showing the temporal positions of the video inputted to the video input section 42, and the timeline TL 3 schematically showing the temporal positions of the video inputted to the video input section 43.

In the modification, the videos inputted to the video input section 41 are the output videos S1, S3, the video inputted to the video input section 42 is the output video S2, and the video inputted to the video input section 43 is the output video S3. Therefore, substantially, the timeline TL1 shows the temporal positions of the output videos S1, S3, the timeline TL2 shows the temporal positions of the output video S2, and the timeline TL3 shows the temporal positions of the output video S3.

In addition, FIG. 9 shows the temporal positions of the editing points with the triangles. The relation between the timings Ta, Tb, Tc, Td, Te, and Tf and the editing points "Index A", "Index B", "Index C", "Index D", "Index E", and "END" is the same as that described with reference to FIG. 6. Note that, in FIG. 9, "Index A", "Index B", "Index C", "Index D", and "Index E" are shown simply as "A", "B", "C", "D", and "E", respectively.

In the modification, in particular, the contents of the identification information corresponding to the output videos S1 and S3 change at the timing Tb1. In this case, "Index B1" is imparted, as the editing point indicating the timing Tb1, to the data of the output videos S1 and S3. Note that "Index B1" is shown simply as "B1" in FIG. 9.

In addition, the contents of the identification information corresponding to the output videos S1 and S3 change at the timing Tb2. In this case, "Index B2" is imparted, as the editing point indicating the timing Tb2, to the data of the output videos S1 and S3. Note that "Index B2" is shown simply as "B2" in FIG. 9.

In the modification, between the timing Tb and the timing Tc, the input source of the output video remains as the input terminal ("SDI 1") of the video input section 41. However, at the timing Tb1 between the timing Tb and the timing Tc, the gamma value is changed from the value ("Endoscope 1") corresponding to the first endoscope 110 to the value ("Endoscope 2") corresponding to the second endoscope 120. In this case, the control section 13 controls the recording section 11 and the storage section 12, so as to impart the editing point "Index B1" to the data of the output videos S1, S3 by regarding the timing at which the gamma value is changed as the timing at which the contents of the identification information change.

Similarly, at the timing Tb2 between the timing Tb and the timing Tc, the gamma value is changed from the value ("Endoscope 2") corresponding to the second endoscope 120 to the value ("Endoscope 1") corresponding to the first endoscope 110. In this case, the control section 13 controls the recording section 11 and the storage section 12, so as to impart the editing point "Index B2" to the data of the output videos S1 and S3 by regarding the timing at which the gamma value is changed as the timing at which the contents of the identification information change.

In addition, in the modification, the information indicating the first endoscope 110 ("surgical endoscope") is added, as the information on the output source, to the data of the output video S1 in the period from the timing Tb to the timing Tb1, the information indicating the second endoscope 120 ("gastrointestinal endoscope") is added, as the information on the output source, to the data of the output video S1 in the period from the timing Tb1 to the timing Tb2, and the information indicating the first endoscope 110 ("surgical endoscope") is added, as the information on the output source, to the data of the output video S1 in the period from the timing Tb2 to the timing Tc.

The present invention is not limited to the above-described embodiment, but various changes, modifications, and the like are possible without changing the gist of the present invention.

What is claimed is:

1. An image recording apparatus comprising:
   a processor comprising hardware, the processor being configured to:
   record a plurality of output videos outputted from a plurality of video output apparatuses, and generate recording information including data of the plurality of output videos, to retain the generated recording information;
   store display state information outputted from a display apparatus configured to display the plurality of output videos, the display state information relating to change points of display states of the plurality of output videos in the display apparatus; and
   generate the recording information by associating the data of the plurality of output videos with the display state information,
   wherein the display state information includes identification information for identifying an output video that is displayed on the display apparatus, among the plurality of output videos, and the processor identifies at least one timing at which a content of the identification information changes, and imparts at least one editing point indicating the at least one timing to data of at least one output video corresponding to the changed content of the identification information, among the data of the plurality of output videos.

2. The image recording apparatus according to claim 1, wherein
the display state information includes a plurality of pieces of setting value information for identifying the plurality of video output apparatuses, and
the processor is further configured to store a table showing a correspondence between the plurality of video output apparatuses and the plurality of pieces of setting value information, and
the processor identifies an output source of each of the plurality of output videos using the table, and adds information on the identified output source to data of each of the plurality of output videos.

3. The image recording apparatus according to claim 1, wherein
the processor outputs at least a part of the recording information to the display apparatus such that the plurality of output videos are displayed on the display apparatus in a display state which is the same as at least a part of the display state when generating the recording information.

4. The image recording apparatus according to claim 1, wherein
the processor generates a recording video corresponding to a video displayed on the display apparatus when generating the recording information by using the plurality of output videos and at least a part of the display state information.

5. The image recording apparatus according to claim 1, wherein
the display state information includes information on an input source of each of the plurality of videos in the display apparatus, information on a correction parameter of each of the plurality of output videos in the display apparatus, and information on a display style of each of the plurality of output videos in the display apparatus.

6. The image recording apparatus according to claim 1, wherein
the processor generates the recording information by associating the data of the plurality of output videos with time information having a correspondence with a lapse of time, and stores the display state information in association with the time information.

7. The image recording apparatus according to claim 1, wherein
the plurality of video output apparatuses is selected from a group of a plurality of apparatuses including a plurality of medical modalities each of which is configured to generate a medical image for diagnosis, and a medical image management apparatus configured to manage the medical images.

8. The image recording apparatus according to claim 1, wherein
the processor outputs at least a part of the recording information to the display apparatus such that a display image, the at least one editing point, and the at least part of the display state information are displayed on the display apparatus, the display image corresponding to at least one output video of the plurality of output videos, the at least one output video being selected by predetermined indicator means.

9. The image recording apparatus according to claim 8, wherein
the processor outputs the data of the plurality of output videos to the display apparatus such that a plurality of timelines, one or more first type of markers, and a plurality of second type of markers are displayed on the display apparatus, each of the plurality of timelines substantially indicating a temporal position of each of the plurality of output videos, the one or more first type of markers indicating the at least one editing point, each of the plurality of second type of markers indicating a time range during which each of the plurality of output videos was being displayed on the display apparatus when generating the recording information,
the predetermined indicator means is means that selects any temporal position on the plurality of timelines and selects the at least one output video that was being displayed on the display apparatus in a timing corresponding to the selected temporal position, and
the display image is an image of the at least one output video that was being displayed on the display apparatus in the timing.

10. A recording method for recording output video signals from video output apparatuses, the recording method comprising:
recording a plurality of output videos outputted from a plurality of video output apparatuses, and generating recording information including data of the plurality of output videos, to retain the generated recording information;
storing display state information outputted from a display apparatus configured to display the plurality of output videos, the display state information relating to change points of display states of the plurality of output videos in the display apparatus; and
generating the recording information by associating the data of the plurality of output videos with the display state information,
wherein the display state information includes identification information for identifying, among the plurality of output videos, the output video that is displayed on the display apparatus, and
the recording method further comprises:
identifying at least one timing at which a content of the identification information changes, and imparting at least one editing point indicating the at least one timing to data of at least one output video corresponding to the changed content of the identification information, among the data of the plurality of output videos.

11. An image recording system comprising:
video output apparatuses that output video signals,
a processor that processes the video signals, and
a display apparatus that displays output videos outputted from the processor, the processor being configured to:
record a plurality of output videos outputted from a plurality of video output apparatuses, and generate recording information including data of the plurality of output videos, to retain the generated recording information;
store display state information outputted from the display apparatus, the display state information relating to change points of display states of the plurality of output videos in the display apparatus; and generate the recording information by associating the data of the plurality of output videos with the display state information, wherein the display state information includes identification information for identifying, among the plurality of output videos, the output video that is displayed on the display apparatus, and the processor is further configured to identify at least one timing at which a content of the identification information changes, and impart at least one editing point indicating the at least one timing to data of at least one output video corresponding to the changed content of the identification information, among the data of the plurality of output videos.

12. An image recording apparatus comprising:

a processor comprising hardware, the processor being configured to:

record a plurality of output videos outputted from a plurality of video output apparatuses, and generate recording information including data of the plurality of output videos, to retain the generated recording information;

store display state information outputted from a display apparatus configured to display the plurality of output videos, the display state information relating to change points of display states of the plurality of output videos in the display apparatus; and generate the recording information by associating the data of the plurality of output videos with the display state information, wherein the display state information includes a plurality of pieces of setting value information for identifying the plurality of video output apparatuses, the processor is further configured to store a table showing a correspondence between the plurality of video output apparatuses and the plurality of pieces of setting value information, and the processor identifies an output source of each of the plurality of output videos using the table, and adds information on the identified output source to data of each of the plurality of output videos.

13. An image recording apparatus comprising:

a processor comprising hardware, the processor being configured to:

record a plurality of output videos outputted from a plurality of video output apparatuses, and generate recording information including data of the plurality of output videos, to retain the generated recording information;

store display state information outputted from a display apparatus configured to display the plurality of output videos, the display state information relating to change points of display states of the plurality of output videos in the display apparatus; and generate the recording information by associating the data of the plurality of output videos with the display state information, wherein the display state information includes information on an input source of each of the plurality of videos in the display apparatus, information on a correction parameter of each of the plurality of output videos in the display apparatus, and information on a display style of each of the plurality of output videos in the display apparatus.

* * * * *